United States Patent
Ibano et al.

(10) Patent No.: US 11,998,703 B2
(45) Date of Patent: Jun. 4, 2024

(54) HOT-COLD TACTILE PRESENTATION DEVICE, WEARABLE TERMINAL, ITCH-SUPPRESSING DEVICE, ICING DEVICE, MASSAGE DEVICE, ORAL RETAINER, AND TABLEWARE

(71) Applicant: Osaka Heat Cool Inc., Osaka (JP)

(72) Inventors: Kenzo Ibano, Osaka (JP); Tohru Sugahara, Osaka (JP); Yuichi Itoh, Kanagawa (JP); Katsunari Sato, Nara (JP); Shintaro Izumi, Kobe (JP)

(73) Assignee: OSAKA HEAT COOL INC., Osaka (JP)

( * ) Notice: Subject to any disclaimer, the term of this patent is extended or adjusted under 35 U.S.C. 154(b) by 0 days.

(21) Appl. No.: 18/273,394

(22) PCT Filed: Dec. 17, 2021

(86) PCT No.: PCT/JP2021/046685
§ 371 (c)(1),
(2) Date: Jul. 20, 2023

(87) PCT Pub. No.: WO2022/158196
PCT Pub. Date: Jul. 28, 2022

(65) Prior Publication Data
US 2024/0042163 A1    Feb. 8, 2024

(30) Foreign Application Priority Data

Jan. 25, 2021    (JP) ................... 2021-009579

(51) Int. Cl.
*A61M 21/00*    (2006.01)
*G08B 6/00*    (2006.01)

(52) U.S. Cl.
CPC ..... *A61M 21/00* (2013.01); *A61M 2021/0022* (2013.01); *A61M 2021/0066* (2013.01);
(Continued)

(58) Field of Classification Search
CPC .............. A61M 2021/0066; A61M 2205/3673
See application file for complete search history.

(56) References Cited

U.S. PATENT DOCUMENTS

| | | | |
|---|---|---|---|
| 4,860,748 A * | 8/1989 | Chiurco ................. | A61F 7/007 607/96 |
| 11,033,750 B1 * | 6/2021 | Radmand ............. | A61N 1/0548 |

(Continued)

FOREIGN PATENT DOCUMENTS

| | | |
|---|---|---|
| JP | H07-072018 A | 3/1991 |
| JP | 2000-33033 A | 2/2000 |

(Continued)

OTHER PUBLICATIONS

International Search Report issued in International Patent Application No. PCT/JP2021/046685, dated Mar. 1, 2022, along with an English translation thereof.

(Continued)

*Primary Examiner* — Thaddeus B Cox

(74) *Attorney, Agent, or Firm* — Greenblum & Bernstein, P.L.C.

(57) ABSTRACT

A hot-cold tactile presentation device includes a plurality of thermoelectric elements which are arranged in a matrix by placing the thermoelectric elements side by side along x and y directions respectively, a plurality of row_heat lines each extending in the x direction, and a plurality of column lines each extending in the y direction. The plurality of row_heat lines are each connected to one end of each of the plurality of thermoelectric elements that align in the x direction, and the plurality of column lines are each connected to the other end of each of the plurality of thermoelectric elements that align in the y direction.

14 Claims, 10 Drawing Sheets

(52) U.S. Cl.
CPC ............... *A61M 2205/3673* (2013.01); *A61M 2209/088* (2013.01); *A61M 2210/0625* (2013.01); *G08B 6/00* (2013.01)

(56) References Cited

U.S. PATENT DOCUMENTS

| | | | | |
|---|---|---|---|---|
| 2008/0287839 | A1* | 11/2008 | Rosen | A61H 9/005 601/18 |
| 2011/0056215 | A1* | 3/2011 | Ham | H01F 38/14 236/51 |
| 2017/0068291 | A1* | 3/2017 | Cheng | H10N 10/10 |
| 2018/0169994 | A1 | 6/2018 | Burwell et al. | |
| 2019/0000599 | A1* | 1/2019 | Hanuschik | A46B 11/00 |
| 2020/0345971 | A1* | 11/2020 | Schirm | A61F 7/02 |
| 2022/0171464 | A1* | 6/2022 | Ollier | G06F 3/016 |

FOREIGN PATENT DOCUMENTS

| | | | |
|---|---|---|---|
| JP | 2001-238903 A | | 9/2001 |
| JP | 2010-171180 A | | 8/2010 |
| JP | 2011-180678 A | | 9/2011 |
| JP | 3216710 U | | 5/2018 |
| JP | 2019-003470 A | | 1/2019 |
| JP | 2020-75130 A | | 5/2020 |
| JP | 7113586 B1 | | 7/2022 |
| KR | 2005-0078889 A | | 8/2005 |
| KR | 10-2017-0028560 A | | 3/2017 |
| KR | 20190038201 A | * | 4/2019 |

OTHER PUBLICATIONS

Notice of Reasons for Refusal issued in Japanese Patent Application No. 2022-515935, dated May 24, 2022, along with an English translation thereof.
Decision to Grant a Patent issued in Japanese Patent Application No. 2022-515935, dated Jun. 28, 2022, along with an English translation thereof.
A. D. Craig and M. C. Bushnell "The Thermal Grill Illusion: Unmasking the Burn of Cold Pain", Science, Jul. 8, 1994, vol. 265, p. 252-255.
Written Opinion of the International Search Authority issued in International Patent Application No. PCT/JP2021/046685, dated Feb. 18, 2022.

* cited by examiner (a)

(b)

(a)

(b)

(a)

(b)

(c)

HOT-COLD TACTILE PRESENTATION DEVICE, WEARABLE TERMINAL, ITCH-SUPPRESSING DEVICE, ICING DEVICE, MASSAGE DEVICE, ORAL RETAINER, AND TABLEWARE

FIELD OF THE INVENTION

The present invention relates to a hot-cold tactile presentation device, a wearable terminal, an itch-suppressing device, an icing device, a massage device, an oral retainer, and a tableware.

BACKGROUND OF THE INVENTION

A hot-cold tactile presentation device that is configured by a thermoelectric element such as a Peltier element is known. When this type of device is incorporated into a user terminal such as a cellular telephone and a wearable terminal, information can be transmitted to a user by a hot-cold sensation which has higher awareness compared to audiovisual or vibration sense.

Patent Literatures 1 and 2 disclose examples of such user terminals. A user terminal described in Patent Literature 1 is a glove-type terminal which is used to transmit temperature information of a virtually contacted object to a user, and is configured to include a single heating element or a combination of a heating element and a cooling element on a fingertip. A user terminal described in Patent Literature 2 is a cellular telephone that notifies of an incoming call by a temperature change and is configured to include a Peltier element on a side face.

Patent Literature 3 discloses a technology of heating or cooling a user's hand by using a plurality of Peltier elements arranged behind a rear cover of a cellular phone terminal, and thereby improving operability of the cellular phone terminal. Patent Literature 3 also discloses making a target temperature variable by performing variable control of the number of Peltier elements that operate simultaneously.

Patent Literature 4 discloses a technology of warming the wrist of a user with rheumatism by attaching four Peltier elements arranged in a 2×2 matrix to a wrist belt.

Non-patent Literature 1 discloses that while humans do not feel pain when cold or hot stimulus is given alone, humans feel pain when cold and hot stimuli are given simultaneously.

RELATED ART

Patent Literature

Patent Literature 1: Japanese Patent Laid-open Publication No. 2019-003470
Patent Literature 2: Republic of Korea Patent Publication No. 2005-0078889 Specification
Patent Literature 3: Japanese Patent Laid-open Publication No. 2010-171180
Patent Literature 4: Japanese Patent Laid-open Publication No. 2001-238903

Non-Patent Literature

Non-patent Literature 1: A. D. Craig and M. C. Bushnell "The Thermal Grill Illusion: Unmasking the Burn of Cold Pain", SCIENCE, Jul. 8, 1994, VOL. 265, p. 252-255

SUMMARY OF THE INVENTION

Problems to be Solved by the Invention

According to the user terminals described in Patent Literatures 1 and 2, only one type of temperature information can be transmitted at the same time. In this situation, since the information that can be transmitted by the hot-cold sensation is limited, the inventors of the present application are investigating configuring a hot-cold tactile presentation device with a plurality of Peltier elements which controls each of the Peltier elements separately, and thereby enables a plurality of temperature information to be simultaneously transmitted to a user.

Here, Patent Literatures 3 and 4 disclose providing a plurality of Peltier elements in a single device, though the goal is not transmitting temperature information. However, even with the technologies described in the literature above, a plurality of temperature information cannot be simultaneously transmitted to a user.

Accordingly, one of the goals for the present invention is to provide a hot-cold tactile presentation device, a wearable terminal, an itch-suppressing device, an icing device, a massage device, an oral retainer and a tableware that can simultaneously transmit more than one temperature information to a user.

Means for Solving the Problems

A hot-cold tactile presentation device according to the present invention includes a plurality of thermoelectric elements arranged in a matrix by placing the thermoelectric elements side by side along a first and a second direction respectively, a plurality of first row lines each extending in the first direction, and a plurality of column lines each extending in the second direction, and the plurality of first row lines are each connected to one end of each of the plurality of thermoelectric elements that align in the first direction and the plurality of column lines are each connected to the other end of each of the plurality of thermoelectric elements that align in the second direction.

A wearable terminal according to an aspect of the present invention is a wearable terminal that includes the hot-cold tactile presentation device.

A wearable terminal according to another aspect of the present invention includes a plurality of thermoelectric elements arranged in a matrix by placing the thermoelectric elements side by side along a first and a second direction respectively, a plurality of first row lines each extending in the first direction, a plurality of column lines each extending in the second direction, and a plurality of second row lines each extending in the first direction. The wearable terminal includes a hot-cold tactile presentation device with each of the plurality of first row lines connected to one end of each of the plurality of thermoelectric elements that align in the first direction, each of the plurality second row lines connected to one end of each of the plurality of thermoelectric elements that align in the first direction, and the plurality of column lines each connected to the other end of each of the plurality of thermoelectric elements that align in the second direction; a first driver circuit that applies one of a power supply potential and a ground potential to one of the first row line and the second row line; and a second driver circuit that applies the other of the power supply potential and ground potential to the column line.

The itch-suppressing device according to the present invention is an itch-suppressing device that includes the hot-cold tactile presentation device.

The icing device according to the present invention is an icing device that includes the hot-cold tactile presentation device.

The massage device according to the present invention is a massage device that includes the hot-cold tactile presentation device.

The oral retainer according to the present invention is an oral retainer that includes the hot-cold tactile presentation device.

The tableware according to the present invention is a tableware that includes the hot-cold tactile presentation device.

Effect of the Invention

According to the present invention, the temperature of each thermoelectric element can be controlled through a combination of the row lines and the column lines, and therefore a plurality of temperature information can be simultaneously transmitted to a user.

MODE FOR CARRYING OUT THE INVENTION

Hereafter, an embodiment of the present invention is described in detail with reference to the attached drawings.

Figure 1:
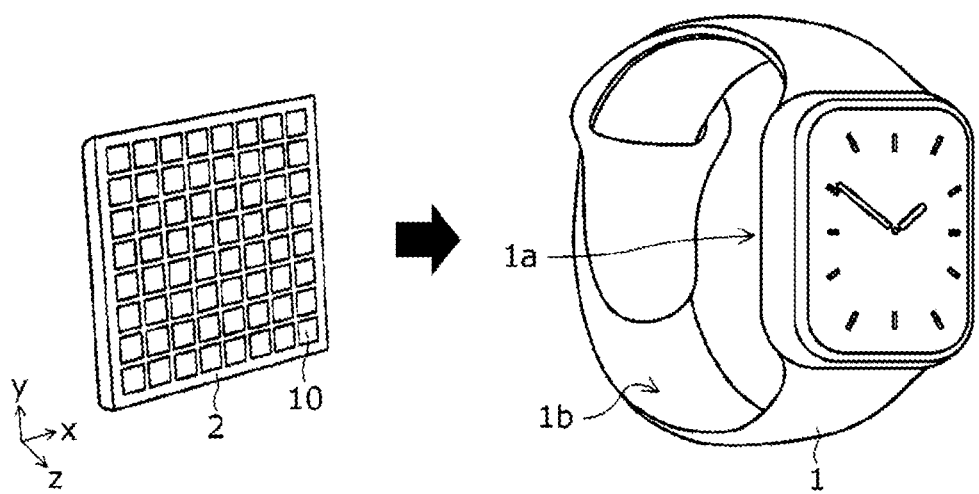
FIG. 1 illustrates a wearable terminal 1 and a hot-cold tactile presentation device 2 according to an embodiment of the present invention.

FIG. 1 illustrates a wearable terminal 1 and a hot-cold tactile presentation device 2 according to the present embodiment. The wearable terminal 1 is a smartwatch, for example, and includes a portion that contacts a user, such as a back surface of a watch face 1a and an inner surface 1b of a band. As the wearable terminal 1 according to the present embodiment, a terminal other than the smartwatch such as a head-mounted display or smart glasses may of course be used. In addition, the wearable terminal 1 may be configured as a device separate from a device with computing function such as a smartphone, and the wearable terminal 1 may be controlled from the device with computing function.

The hot-cold tactile presentation device 2 is a device that includes a plurality of thermoelectric elements 10 arranged in a matrix. As shown in FIG. 1, each thermoelectric element 10 is placed side by side on a substrate with flexibility such as a flexible substrate or a stretchable substrate, along an x direction and y direction respectively and at intervals in the x direction and y direction respectively. In this way, since each thermoelectric element 10 is arranged on the substrate with flexibility at intervals and each thermoelectric element 10 is also flexible as noted below, the hot-cold tactile presentation device 2 has high flexibility and is configured to be bendable in a z direction. Using this flexibility, the hot-cold tactile presentation device 2 is incorporated into any portion of the wearable terminal 1 that is in contact with the user, such as the back surface 1a and the inner surface 1b noted above.

Figure 2:
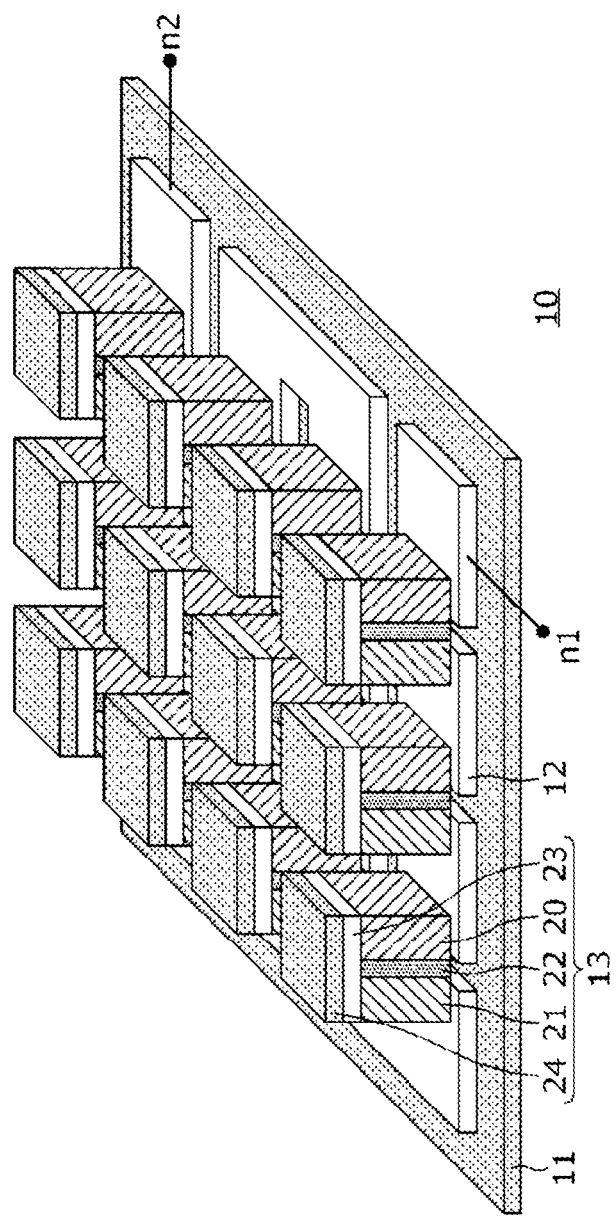
FIG. 2 illustrates a structure of an individual thermoelectric element 10.

FIG. 2 illustrates a structure of an individual thermoelectric element 10. As shown in FIG. 2, the thermoelectric element 10 is configured to include a substrate 11 which is a flexible substrate made of an insulator such as polyimide or a stretchable substrate made of an elastic polymer material such as an elastomer; a plurality of electrodes 12 arranged at intervals on the substrate 11; and a plurality of unit thermoelectric elements 13 arranged to span the top surfaces of two adjacent electrodes 12.

Nodes n1, n2 illustrated in FIG. 2 are each an external terminal of the thermoelectric element 10, and each electrode 12 is arranged in a line at equal intervals between the nodes n1 and n2. As understood from FIG. 2, a column configured by each electrode 12 (hereafter referred to as a "electrode line") is not in a straight line, but in zigzag on the substrate 11 such that each unit thermoelectric element 13 is arranged in a matrix.

Each of the unit thermoelectric elements 13 is configured to include an n-type semiconductor 20 bonded using conductive paste to a first of the two adjacent electrodes 12 which is located closer to the node n1 within the electrode line; a p-type semiconductor 21 bonded using conductive paste to a second of the two adjacent electrodes 12 which is located closer to the node n2 within the electrode line; an insulator 22 placed between the n-type semiconductor 20 and the p-type semiconductor 21 and electrically separates them; an electrode 23 bonded to a top surface (surface opposite of the substrate 11) of the n-type semiconductor 20, the p-type semiconductor 21, and the insulator 22 using conductive paste and the like; and a substrate 24 covering the top surface of the electrode 23. The substrate 24 is a flexible substrate made of an insulator such as polyimide finely cut by a laser or the like. Each of the unit thermoelectric elements 13 is arranged at intervals, and as a result, the thermoelectric element 10 is provided with high flexibility. In addition, a space between respective unit thermoelectric elements 13 is electrically connected via the electrode line, and is otherwise electrically disconnected.

With the above configuration, the temperature of the electrode 23 and the substrate 24 increases when electric current flows from the node n1 to the node n2 and decreases when the electric current flows from the node n2 to the node n1. Conversely, the temperature of the electrode 12 and the substrate 11 decreases when the electric current flows from the node n1 to the node n2 and increases when the electric current flows from the node n2 to the node n1. The hot-cold tactile presentation device 2 serves to provide, through this temperature change, a hot-cold tactile sense to the skin of the user wearing the wearable terminal 1. When incorporating the hot-cold tactile presentation device 2 into the wearable terminal 1, the hot-cold tactile presentation device 2 may be incorporated such that the substrate 24 side is the user side or incorporated such that the substrate 11 side is the user side, but the description below continues with the substrate 24 side being the user side. In this case, a hot sensation is transmitted to the user when the electric current flows from the node n1 to the node n2, and a cold sensation is transmitted to the user when the electric current flows from the node n2 to the node n1.

Figure 3:
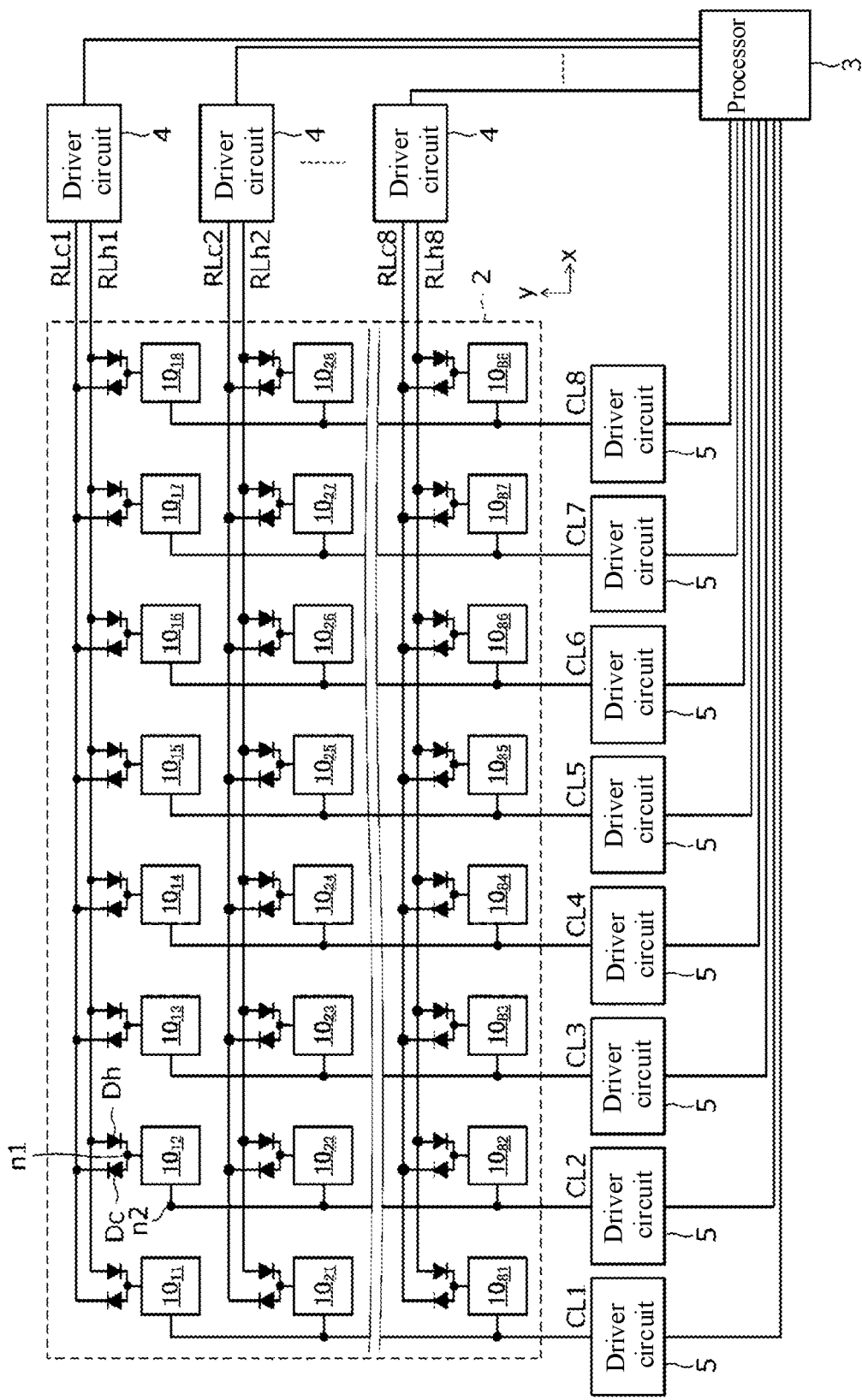
FIG. 3 illustrates a circuit configuration of the wearable terminal 1 and hot-cold tactile presentation device 2.

FIG. 3 illustrates a circuit configuration of the wearable terminal 1 and the hot-cold tactile presentation device 2. As shown in FIG. 3, the hot-cold tactile presentation device 2 is configured to include, in addition to the plurality of thermoelectric elements 10, a plurality of row_heat lines RLh (first row lines) and a plurality of row_cool lines RLc (second row lines) that respectively extend in the x direction, a plurality of column lines CL that each extend in the y direction, a plurality of diodes Dh (first diodes) that are correspondingly provided to each of the plurality of thermoelectric elements 10, and a plurality of diodes Dc (second diodes) that are correspondingly provided to each of the plurality of thermoelectric elements 10.

FIG. 3 shows an example of the hot-cold tactile presentation device 2 that has 64 thermoelectric elements 10 arranged in a matrix of eight rows and eight columns. The number appended to the lower right of each thermoelectric element 10 reference numeral indicates the coordinates of each thermoelectric element 10 in the matrix. However, the arrangement and number of the thermoelectric element 10 is not limited to the eight rows and eight columns with a total of 64, and can be a total of m×n in m rows and n columns ($1 \leq m$, $1 \leq n$).

One each of the row_heat line RLh and row_cool line RLc are provided to each row of the matrix. The row_heat line RLh is connected through the diodes Dh to each of the plurality of thermoelectric elements 10 that are lined up in the corresponding row. The electrode of the diode Dh connected to the row_heat line RLh is an anode. A cathode of the diode Dh is connected to the node n1 of the corresponding thermoelectric element 10. Also, the row_cool line RLc is connected through the diodes Dc to each of the plurality of thermoelectric elements 10 that are lined up in the corresponding row. The electrode of the diode Dc connected to the row_cool line RLc is a cathode. An anode of the diode Dc is connected to the same node n1 as the cathode of the corresponding diode Dh.

One column line CL is provided to each column of the matrix. Each column line CL is commonly connected to the respective node n2 of the plurality of thermoelectric elements 10 that are lined up in the corresponding column.

The wearable terminal 1 is configured to include a single driver circuit 4 (first driver circuit) for each combination of the row_heat line RLh and the row_cool line RLc, a single driver circuit 5 (second driver circuit) for each column line CL, and a processor 3 that controls the driver circuits 4 and 5. Of these, the processor 3 is a central processing unit of the wearable terminal 1 and is configured to execute various processes noted below by retrieving and executing a program from a memory not shown in the drawings. Also, the driver circuits 4 and 5 are each a circuit that controls the electric current flowing through a connected trace in accordance with the control by the processor 3.

Figure 4:
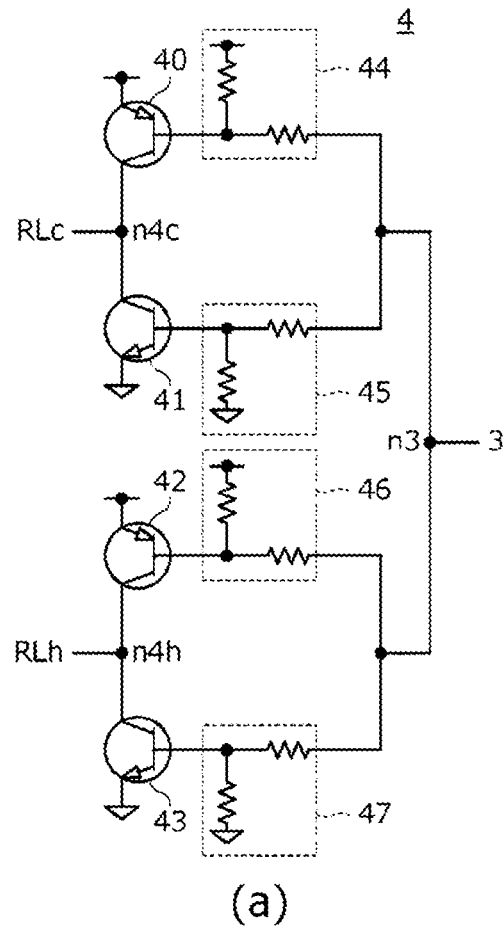
FIG. 4(a) illustrates an internal configuration of a driver circuit 4.
FIG. 4(b) illustrates an internal configuration of a driver circuit 5.
Figure 4:
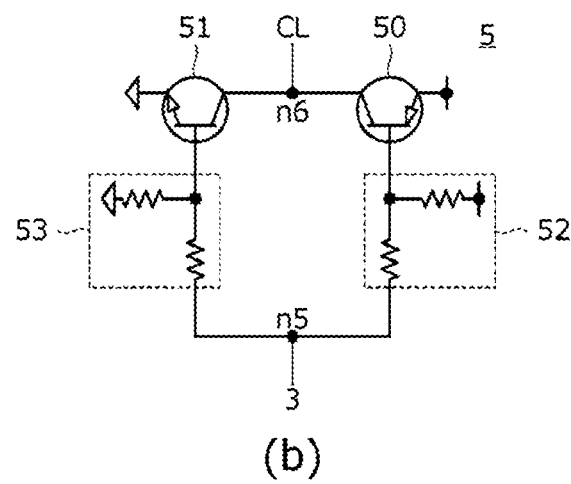

FIG. 4(a) illustrates an internal configuration of the driver circuit 4. As shown in FIG. 4(a), the driver circuit 4 is configured to include transistors 40 to 43 and voltage division circuits 44 to 47. The transistors 40 to 43 are each a bipolar transistor, and the combination of transistors 40 and 41 and the combination of transistors 42 and 43 each configure a collector output-type SEPP (Single Ended Push-Pull). Specifically, the transistors 40 and 42 are configured by a PNP type bipolar transistor and the transistors 41 and 43 are configured by an NPN type bipolar transistor. An emitter of the transistors 40 and 42 is connected to a power supply potential and an emitter of the transistors 41 and 43 is connected to a ground potential. A base of the transistors 40 to 43 is connected, through the respective voltage division circuits 44 to 47, to a node n3 which is an input terminal of each SEPP. A control signal from the processor 3 is supplied to the node n3. Collectors for each of the transistor 40 and transistor 41 are mutually connected and configure a node n4c that is an output terminal of the SEPP configured by the transistors 40 and 41. The node n4c is connected to the corresponding row_cool line RLc. Similarly, collectors for each of the transistor 42 and transistor 43 are mutually connected and configure a node n4h that is an output terminal of the SEPP configured by the transistors 42 and 43. The node n4h is connected to the corresponding row_heat line RLh.

FIG. 4(b) illustrates an internal configuration of the driver circuit 5. As shown in FIG. 4(b), the driver circuit 5 is configured to include transistors 50 and 51 and voltage division circuits 52 and 53. The transistors 50 and 51 are each a bipolar transistor and configure a collector output-type SEPP similarly to the transistors 40 and 41 illustrated in FIG. 4(a). Specifically, the transistor 50 is configured by a PNP type bipolar transistor and the transistor 51 is configured by an NPN type bipolar transistor. An emitter of the transistor 50 is connected to a power supply potential and an emitter of the transistor 51 is connected to a ground potential. A base of the transistors 50 and 51 is connected, through the respective voltage division circuits 52 and 53, to a node n5 which is an input terminal of the SEPP. A control signal from the processor 3 is supplied to the node n5. Collectors for each of the transistor 40 and transistor 41 are mutually connected and configure a node n6 that is an output terminal of the SEPP. The node n6 is connected to the corresponding column line CL.

Figure 5:
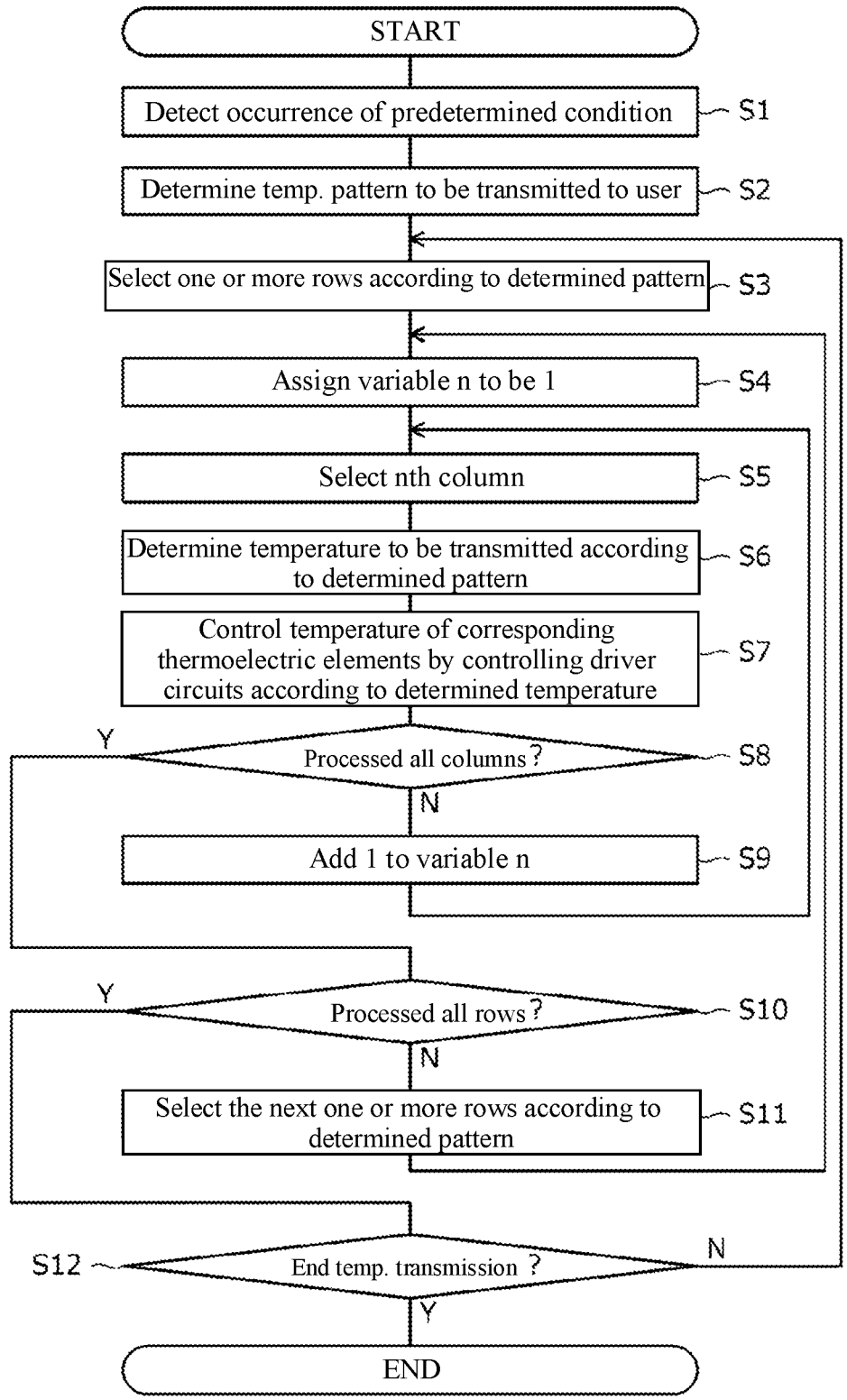
FIG. 5 is a procedural flow chart that illustrates a process executed by a processor 3 that uses the hot-cold tactile presentation device 2 to transmit a hot-cold sensation to a user.

FIG. 5 is a procedural flow chart that illustrates a process executed by the processor 3 that uses the hot-cold tactile presentation device 2 to transmit a hot-cold sensation to the user. Hereafter, a method of transmitting a hot-cold sensation to a user using the hot-cold tactile presentation device 2 is described in detail with reference to FIG. 5.

As shown in FIG. 5, the processor 3 first detects an occurrence of a predetermined condition (step S1). Specific examples of the predetermined condition include, for example, drowsiness while driving, staggering while working, a disaster such as an earthquake or typhoon, an accident in the neighborhood, an incoming call or short message service, a condition that requires information communication in Braille, and the like. The processor 3 may detect drowsiness while driving or staggering while working based on a condition detected by a sensor provided inside or outside of the wearable terminal 1. Further, the processor 3 may detect the occurrence of a disaster or accident by referring to information received from a network service such as an urgent earthquake warning and traffic information.

The processor 3 that has detected the occurrence of the predetermined condition determines, based on the detected condition, a temperature pattern to be transmitted to the user (step S2). Specifically, a table showing an association of the condition and the temperature pattern is stored ahead of time in the memory of the wearable terminal 1, and the processor 3 can determine the temperature pattern by referring to the table based on the detected condition. The temperature pattern determined in step S2 includes one or more temperature distributions in the matrix of the thermoelectric elements 10, the order and number of repetitions of each temperature distribution, the order of row selection, and the like.

Figure 6:
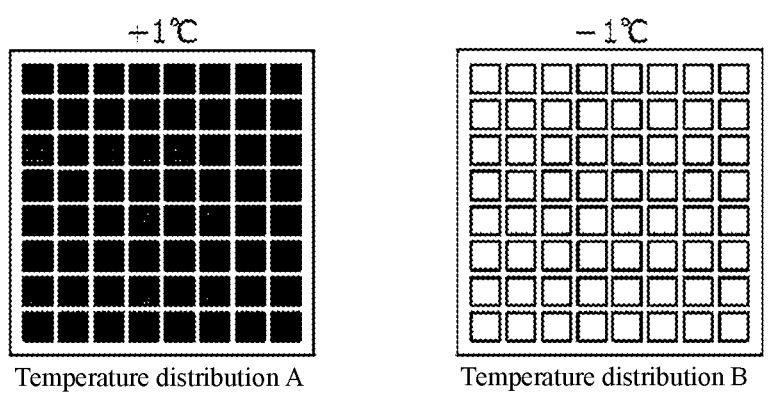
FIG. 6(a) and FIG. 6(b) each illustrate exemplary temperature distributions included in a pattern determined in step S2 of FIG. 5.
Figure 6:
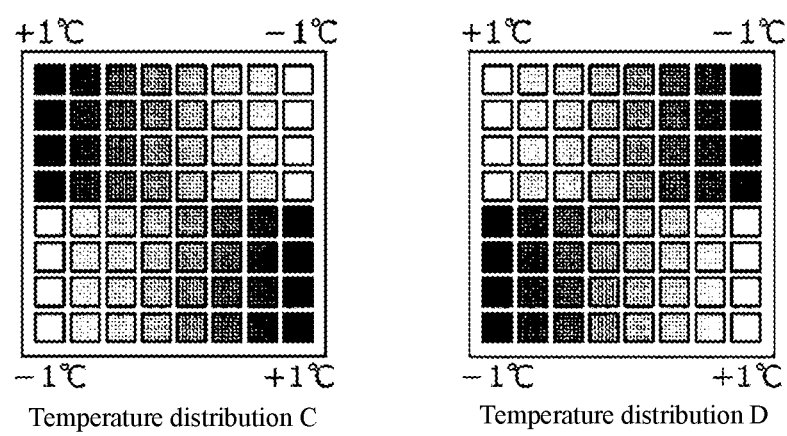

FIGS. 6(a) and 6(b) each illustrate exemplary temperature distributions included in a pattern determined in step S2. The pattern shown in FIG. 6(a) is a pattern that is favorably used to warn the user of dangerous conditions such as drowsiness while driving, staggering while working, a disaster such as an earthquake or typhoon, or an accident in the neighborhood, and is configured to alternatingly reproduce a temperature distribution A and temperature distribution B illustrated in the drawing at predetermined time intervals. The temperature distribution A raises the temperature of all thermoelectric elements 10 by one degree, and the temperature distribution B lowers the temperature of all thermoelectric elements 10 by one degree.

The pattern shown in FIG. 6(b) is a pattern that is favorably used to notify of an incoming call and short message service, and is configured to alternatingly reproduce a temperature distribution C and temperature distribution D illustrated in the drawing at predetermined time intervals. The temperature distribution C sets a temperature for rows in an upper half at equal temperature intervals from +1° C. to −1° C. from the left end column toward the right end column, and sets a temperature for rows in a bottom half at equal temperature intervals from −1° C. to +1° C. from the left end column toward the right end column. In the temperature distribution D, the temperature distribution C is inverted vertically (or horizontally).

Various patterns are possible as the pattern determined in step S2 in addition to the patterns shown in FIGS. 6(a) and 6(b). For example, it is possible to transmit text data one character at a time using the temperature distribution such as in Braille. By transmitting information through the hot-cold sensation in this way, information can be transmitted with higher awareness compared to audiovisual or vibration. Also, unlike transmitting audiovisual or vibration, there is little risk of transmitting information to anyone other than the person wearing the wearable terminal 1, and therefore allows a high level of confidentiality to be preserved.

Back to FIG. 5. The processor 3 that has determined the temperature pattern first selects one or more rows according to the determined pattern (step S3). In this selection, one or more rows that are controlled by the same temperature distribution are selected in one-row units. For example, all eight rows are selected in the temperature distributions A and B of FIG. 6(a). On the other hand, the top four rows or the bottom four rows are selected in the temperature distributions C and D in FIG. 6(b). In step S3, one row may of course also be selected.

Next, the processor 3 assigns a variable n to be 1 (step S4) and selects the nth column (step S5). Then, according to the determined pattern, the temperature to be transmitted by one or more thermoelectric elements 10 corresponding to the selected row and column is determined (step S6). As an example, when a description is given of a case where the temperature distribution C illustrated in FIG. 6(b) is being reproduced and the rows selected in step S3 (or step S11 described later) are the top four rows, the temperature determined in step S6 is +1° C. when the selected column is the far-left column. Also, when the selected column is the far-right column, the temperature determined in step S6 is −1° C. Further, when the selected column is the second column from the left, the temperature determined in step S6 is +0.71 (≅1−2/7) ° C.

Next, the processor 3 controls the temperature of the corresponding thermoelectric elements 10 by controlling the driver circuits 4 and 5 according to the determined temperature (step S7). Specifically, when the determined temperature is positive, the processor 3 controls the driver circuits 4 and 5 such that the electric current flows from the corresponding row_heat line RLh toward the corresponding column line CL. In other words, the driver circuits 4 and 5 are controlled such that the transistor 42 illustrated in FIG. 4(a) and the transistor 51 illustrated in FIG. 4(b) are each on, and the transistor 43 illustrated in FIG. 4(a) and the transistor 50 illustrated in FIG. 4(b) are each off. At this time, the transistor 40 illustrated in FIG. 4(a) is also on, but no current flows to the corresponding row_cool line RLc due to the presence of the diode Dc. Accordingly, since the electric current flows from the node n1 toward the node n2 in the corresponding thermoelectric element 10, the temperature of the thermoelectric element 10 is raised and the hot sensation can be transmitted to the user. In this case, the processor 3 realizes an arbitrary temperature by appropriately controlling voltage between the base and emitter of the transistors 42 and 51 and controlling the magnitude of electric current flowing in the thermoelectric element 10.

In addition, when the determined temperature is negative, the processor 3 controls the driver circuits 4 and 5 such that the electric current flows from the corresponding column line CL toward the corresponding row_cool line RLc. In other words, the driver circuits 4 and 5 are controlled such that the transistor 41 illustrated in FIG. 4(a) and the transistor 50 illustrated in FIG. 4(b) are each on, and the transistor 41 illustrated in FIG. 4(a) and the transistor 51 illustrated in FIG. 4(b) are each off. At this time, the transistor 43 illustrated in FIG. 4(a) is also on, but no current flows to the corresponding row_heat line RLh due to the presence of the diode Dh. Accordingly, since the electric current flows from the node n2 toward the node n1 in the corresponding thermoelectric element 10, the temperature of the thermoelectric element 10 is lowered and the cold sensation can be transmitted to the user. In this case, the processor 3 realizes an arbitrary temperature by appropriately controlling voltage between the base and emitter of the transistors 41 and 50 and controlling the magnitude of electric current flowing in the thermoelectric element 10.

Next, the processor 3 determines whether all columns are processed (step S8). When the processor 3 determines that the columns are not processed at this point, 1 is added to the variable n (step S9) and the process returns to step S5. By repeating this process, all columns are processed in order.

When the processor 3 determines that all columns are processed in step S8, the processor 3 then determines whether all rows are processed (step S10). When the processor 3 determines that the rows are not processed at this point, the next one or more rows are selected according to the pattern determined in step S2 (step S11) and the process returns to step S4. For example, when the temperature distribution C illustrated in FIG. 6(b) is being reproduced and the top four rows are selected in step S3, the processor 3 selects the bottom four rows in step S11. In addition, when one row is selected in step S3, the processor 3 selects in current step S11 the rows that have not yet been selected in step S3 and in the previous step S11 executed after step S3.

After determining that all rows are processed in step S10, the processor 3 follows the pattern determined in step S2 and determines whether to end a temperature transmission (step S12). The result of the determination is affirmative when the number of reproductions of the respective temperature distribution included in the pattern determined in step S2 reaches the number of repetitions included in the same pattern. The processor 3 that obtained the affirmative determination result in step S12 ends the process of transmitting the hot-cold sensation to the user. On the other hand, the processor 3 that obtained a negative determination result in step S12 continues the process by returning to step S3.

As described above, according to the wearable terminal 1 and the hot-cold tactile presentation device 2 of the present embodiment, the temperature of each thermoelectric element 10 can be controlled while avoiding a snake path described below, through a combination of the row_cool line RLc or the row_heat line RLh and the column line CL, and therefore, more than one temperature information can be simultaneously transmitted to the user. In addition, when a head-mounted display is used as the wearable terminal 1 for example, by simultaneously transmitting more than one temperature information to the user, a sense of immersion into a virtual reality experience can also be improved.

Figure 7:
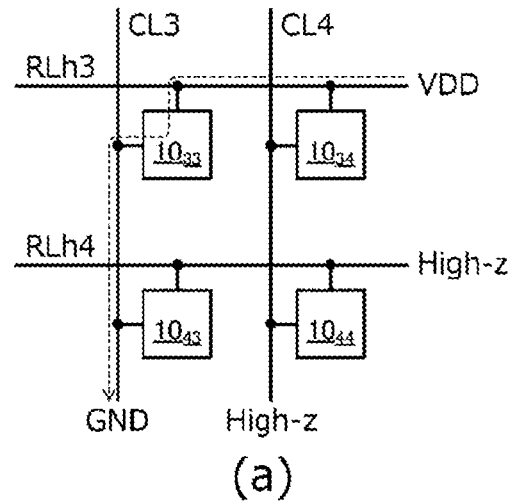
FIG. 7(a), FIG. 7(b) and FIG. 7(c) are each an explanatory diagram of a snake path.
Figure 7:
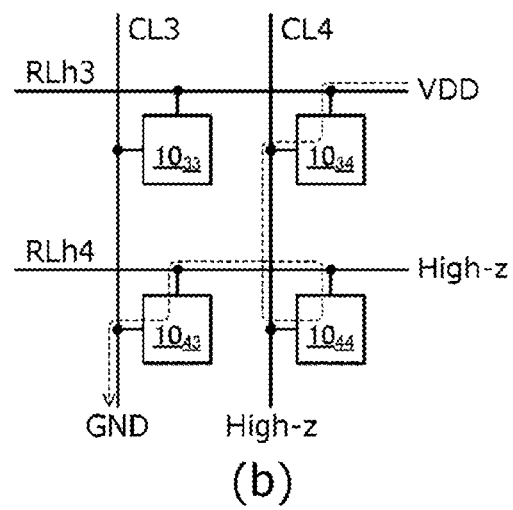
Figure 7:
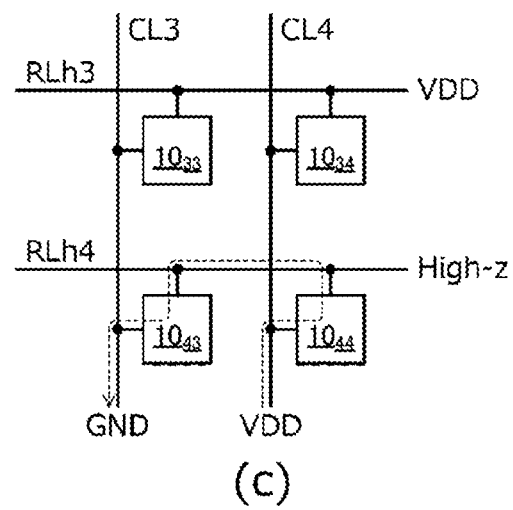

Here, the snake path is described. FIGS. 7($a$), 7($b$) and 7($c$) each include an explanatory diagram of the snake path and shows four thermoelectric elements $10_{33}$, $10_{34}$, $10_{43}$, and $10_{44}$ of the plurality of thermoelectric elements 10 that configure the hot-cold tactile presentation device 2, and corresponding row_heat lines RLh3 and RLh4 and column lines CL3 and CL4. However, FIGS. 7($a$), 7($b$) and 7($c$) each show a case without the diode Dh.

When the thermoelectric element $10_{33}$ is subject to temperature control, the processor 3 must supply the electric current shown by a dashed line in FIG. 7($a$). In order to accomplish this, as shown in FIG. 7($a$), when the processor 3 uses the driver circuits 4 and 5 to apply a power supply potential VDD to the row_heat line RLh3, apply a ground potential GND to the column line CL3, and put the other row_heat line RLh and column line CL in a high impedance (High-z) state, as shown by a dashed line in FIG. 7($b$), the electric current may also flow to thermoelectric elements 10 other than the thermoelectric element $10_{33}$. Even when the power supply potential VDD is applied to the other column line CL as well in order to prevent this, as shown in FIG. 7($c$) for example, the electric current still flows to thermoelectric elements 10 other than the thermoelectric element $10_{33}$, as illustrated in the same drawing. Accordingly, an electric current path that travels through the unintended thermoelectric elements 10 is referred to as the "snake path".

When the snake path is present, controlling each of the thermoelectric elements 10 individually is not possible. Thus, in the hot-cold tactile presentation device 2 according to the present embodiment, the diode Dh is inserted between each row_heat line RLh and each corresponding thermoelectric element 10. Doing this results in avoiding the occurrence of the snake paths illustrated in FIGS. 7($b$) and 7($c$), and enables controlling each of the thermoelectric elements 10 individually. Inserting the diode Dc between each row_cool line RLc and each corresponding thermoelectric element 10 is also for the same reason.

A preferable embodiment of the present invention was described above, but the present invention is not limited in any way to the embodiment noted above, and various forms are, of course, possible without departing from the scope of the present invention.

For example, in the embodiment described above, the hot-cold tactile presentation device 2 configured so as to transmit both hot and cold sensations by providing the row_cool line RLc and row_heat line RLh is described, however, the hot-cold tactile presentation device 2 may be configured so as to transmit only one of the hot or cold sensations by providing only one of the row_cool line RLc or row_heat line RLh. In this case, the driver circuits 4 and 5 need not be provided with the SEPP, and may be configured so as to each include a single bipolar transistor.

In addition, in the embodiment described above, an example is described in which the diode Dc is provided between the row_cool line RLc and the thermoelectric element 10, and the diode Dh is provided between the row_heat line RLh and the thermoelectric element 10, however, a switch element may be provided instead of the diodes Dh and Dc, and ON-OFF control may be performed by the processor 3. Further, the row_cool line RLc and/or row_heat line RLh may also be connected directly to the thermoelectric elements 10, without providing either diodes or a switch element between the row_cool line RLc and each thermoelectric element 10 and/or the row_heat line RLh and each thermoelectric element 10. In this case, forming of the snake path is inevitable, but temperature control is possible to some extent.

In addition, the embodiment described above is given on the assumption that the x direction, y direction, and z direction in FIG. 1 are one-dimensional directions (straight lines) that are mutually orthogonal to each other, however, the x direction, y direction, and z direction need not be orthogonal and may each be a three-dimensional direction (a curve extending within a three-dimensional space). In other words, each thermoelectric element 10 only needs to be electrically arranged in the matrix, and not be physically arranged in a grid pattern.

In addition, in the embodiment described above, an example is described in which the electrode 12 and unit thermoelectric element 13 are mounted onto the substrate 11, however, the substrate 11 may be omitted. In this case, by embedding each electrode 12 and each unit thermoelectric element 13 into an elastomer resin, a three-dimensional configuration may be fixed while ensuring flexibility. Further, the row_heat line RLh, row_cool line RLc, and column line CL may also be embedded into the elastomer resin, and the entire hot-cold tactile presentation device 2 may be fixed with a lump of elastomer resin.

In addition, in the embodiment described above, an example is described in which the present invention is applied to the hot-cold tactile presentation device 2 incorporated in the wearable terminal 1, however, the present invention can also be applied to a hot-cold tactile presentation device that is incorporated into other types of devices. Hereafter, a detailed description is given of modifications to the above-described embodiment that are made for such a device.

Figure 8:
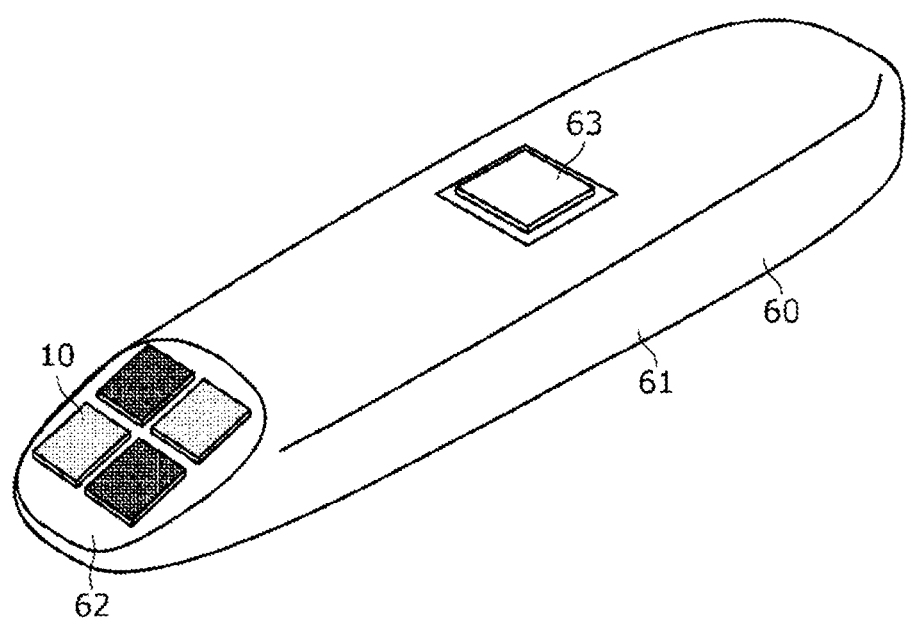
FIG. 8 is a view illustrating an outer appearance of an itch-suppressing device 60 according to a first modification of the embodiment of the present invention.

FIG. 8 is a view illustrating an outer appearance of an itch-suppressing device 60 according to a first modification of the embodiment described above. As shown in FIG. 8, the itch-suppressing device 60 is configured to include a bar-shaped casing 61, a flat portion 62 that is provided to a forefront end of the casing 61, and an electrical power switch 63 that is provided toward the middle of the bar-shaped casing 61. The plurality of thermoelectric elements 10 are arranged in a matrix on a surface of the flat portion 62. Although not shown in FIG. 8, devices (such as the processor 3 and the driver circuits 4 and 5) required to configure the circuit illustrated in FIG. 3 are arranged inside the casing 61.

The itch-suppressing device 60 is a device that serves to reduce itchiness of the user by holding the casing 61 in a hand, turning the electrical power switch 63 on, and applying the flat portion 62 to the user's affected part. When the flat portion 62 is applied to the user's affected part in a state where all of the plurality of thermoelectric elements 10 are heated at the same temperature, the user's itchiness may actually increase. In contrast, when the present invention is used, the temperature of the plurality of thermoelectric elements 10 can be controlled individually as illustrated in FIG. 8, so that cold and hot stimuli can be simultaneously given to the user. Therefore, it is possible to give pain to the user as described in Non-patent Literature 1, and thus the user's itchiness can be reduced according to the itch-suppressing device 60 of the present modification.

In the present modification, an example is described in which four thermoelectric elements 10 are arranged on the flat portion 62, however, at least two thermoelectric elements 10 may be arranged on the flat portion 62. Also, FIG. 8 shows an example in which the cold stimulus is given along first opposing corners of the four thermoelectric elements 10 and the hot stimulus is given along second opposing corners, however the cold and hot stimuli may also be given simultaneously in a different pattern.

In addition, the wearable terminal 1 shown in FIG. 1 can also perform as the itch-suppressing device. In this case, a sensor (such as an acceleration sensor and a gyro sensor) detecting the user's motion is mounted to the wearable terminal 1, the processor 3 executing the processes shown in FIG. 5 detects a predefined scratch motion using the sensor (step S1), and in response to detecting the predefined scratch motion, determines a pattern that can simultaneously give the cold and hot stimuli to the user as the temperature pattern to be transmitted to the user (step S2), and executes the processes in steps S3 to S12 according to the determined pattern. In this example, when the user makes a motion of scratching the surface of the right foot while wearing the wearable terminal 1 on the right hand, for example, the user feels pain on the right hand instead of the surface of the right foot which the user was attempting to scratch, but pain generally exceeds itchiness, and therefore the wearable terminal 1 allows the user to forget the itchiness on the right foot surface, that is, suppress itchiness of the affected part.

Figure 9:
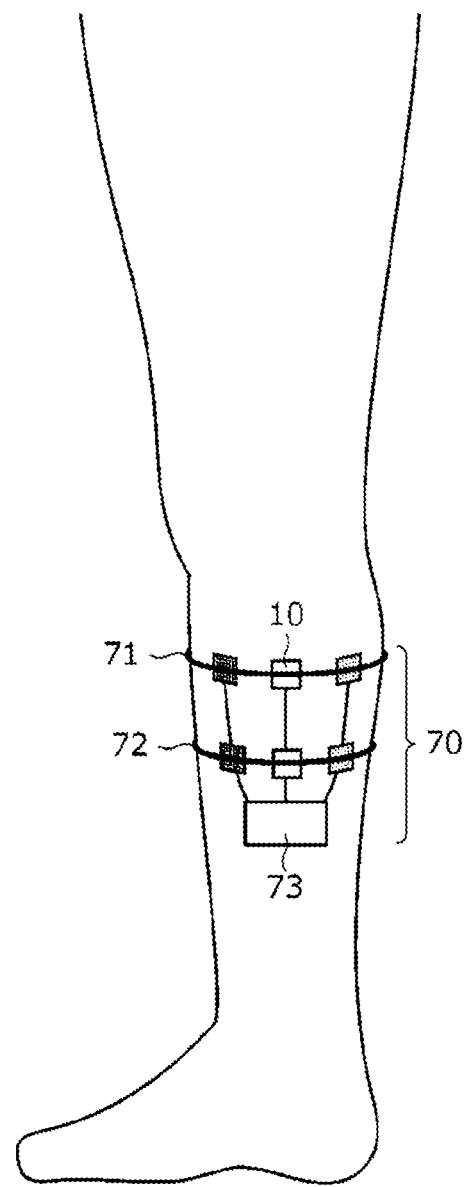
FIG. 9 is a view illustrating a use state of an icing device 70 according to a second modification of the embodiment of the present invention.

FIG. 9 is a view illustrating a use state of an icing device 70 according to a second modification of the embodiment described above. As shown in FIG. 9, the icing device 70 is configured to include two bands 71 and 72, each having the plurality of thermoelectric elements 10 attached thereto in a line, and a circuit portion 73 that is electrically connected to each thermoelectric element 10. Inside the circuit portion 73, devices (such as the processor 3 and the driver circuits 4 and 5) required to configure the circuit illustrated in FIG. 3 are arranged.

The icing device 70 is used with the bands 71 and 72 being mounted on the human calf as shown in FIG. 9, and the basic role thereof is to provide icing to calves exhausted from exercising and the like. When the bands 71 and 72 are mounted on the human calf, each thermoelectric element 10 is attached to the bands 71 and 72 so as to be attached firmly to the human body on the substrate 24 side (or substrate 11 side) illustrated in FIG. 2.

The icing device 70 is a device for icing the calf as described above, but simply lowering the temperature of the thermoelectric elements 10 all at once may have the opposite effect by cooling the body too much. In this regard, when the temperatures of the plurality of thermoelectric elements 10 are individually controlled using the present invention, it is possible to prevent the body from becoming too cold and to also obtain a massage effect by alternately circulating cold and hot stimuli in a circumferential direction of the calf for example. Therefore, according to the icing device 70 of the present modification, fatigue of the calf can be removed more effectively. Further, giving the cold and hot stimuli simultaneously can provide pain as in the first modification to reduce the user's itchiness.

In the present modification, an example of the icing device 70 having two bands 71 and 72 is described, but the icing device 70 may have at least one band. In addition, the number of thermoelectric elements 10 to be attached to each band is not particularly limited, and the icing device 70 may have two or more thermoelectric elements 10 as a whole.

Also, the present modification describes an example in which the present invention is applied to the icing device 70 for use on a calf, however, the present invention can be widely applied to other icing devices or to massage devices that are not for icing. For example, by applying the present invention to a device for icing or massaging an eye (eye mask), ear (headphone), face, neck, back, shoulder, chest, arm, thigh, and the like, icing or massaging these areas effectively is possible. Depending on the area, further benefits such as sleep improvement, meditation improvement, heatstroke prevention, tension relaxation from stimulation to the heart, and the like can be obtained.

Figure 10:
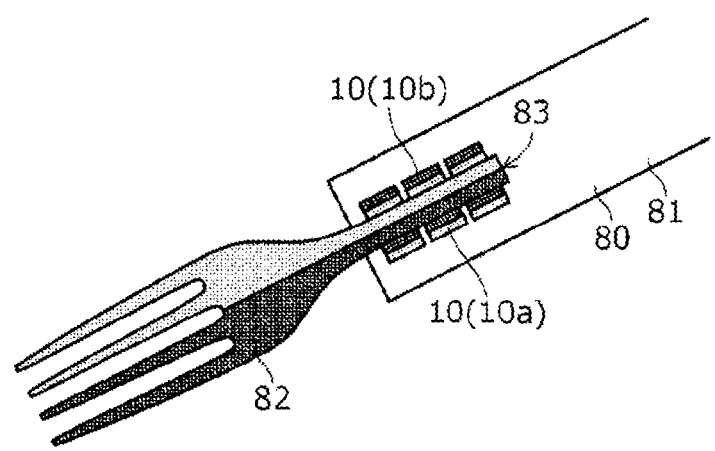
FIG. 10 is a view illustrating an oral retainer 80 according to a third modification of the embodiment of the present invention.

FIG. 10 is a view illustrating an oral retainer 80 according to a third modification of the embodiment described above. As shown in FIG. 10, the oral retainer 80 is a so-called fork, and is configured to include a casing 81 that forms a handle, a comb-like forefront end portion 82 which is mounted to the foremost end of the casing 81, an insulating material 83 provided passing through the center of the comb-like forefront end portion 82 in an axis direction of the oral retainer 80, and the plurality of thermoelectric elements 10 arranged on both sides of the portion of the comb-like forefront end portion 82 that extends inside the casing 81. Each thermoelectric element 10 is arranged so as to be attached firmly to the comb-like forefront end portion 82 on the substrate 24 side (or substrate 11 side) illustrated in FIG. 2. Although the inside of the casing 81 is illustrated in FIG. 10, the casing 81 is an opaque cylindrical member and the configuration inside the casing 81 cannot actually be seen from the outside. In addition, though not shown in FIG. 10, devices (such as the processor 3 and the driver circuits 4 and 5) required to configure the circuit illustrated in FIG. 3 are also arranged inside the casing 81.

Because the insulating material 83 is provided in the center of the comb-like forefront end portion 82, the comb-like forefront end portion 82 is configured to be able to control temperature separately for a first side of the insulating material 83 (simply referred to as "first side") and a second side of the insulating material 83 (simply referred to as "second side"). In addition, the plurality of thermoelectric elements 10 are configured to include one or more first thermoelectric elements 10*a* that are attached firmly to the first side of the comb-like forefront end portion 82 and one or more second thermoelectric elements 10*b* that are attached firmly to the second side of the comb-like forefront end portion 82. Accordingly, by enacting different temperature control for the first thermoelectric element 10*a* and the second thermoelectric element 10b, the cold stimulus can be given to the user on the first side and the hot stimulus can be given to the user on the second side of the comb-like forefront end portion 82, and therefore the user's sense of taste can be manipulated by pain stimulation according to the oral retainer 80 of the present modification.

In the present modification, a description was given of an example in which the present invention was applied to the oral retainer 80 that is a fork, however, the present invention can also be applied to any tool that may be held in the mouth. For example, the present invention can also be applied as in the present modification to other types of silverware such as spoons and chopsticks, straws, and cigarettes. When the present invention is applied to the silverware, the user's sense of taste can be manipulated as described in the present modification. When the present invention is applied to straws and cigarettes, refreshing feeling and aromatic feeling can be improved.

Figure 11:
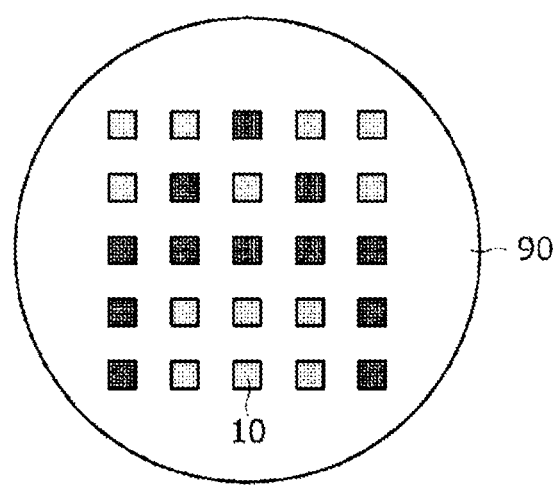
FIG. 11 is a view illustrating a tableware 90 according to a fourth modification of the embodiment of the present invention.

FIG. 11 is a view illustrating a tableware 90 according to a fourth modification of the embodiment described above. As shown in FIG. 11, the tableware 90 is a round plate and is configured to include a plurality of thermoelectric elements 10 arranged in a matrix on a bottom surface. FIG. 11 shows an example of a round tableware 90, however the shape of the tableware 90 is not limited to a round shape. Each thermoelectric element 10 is embedded in the surface of the tableware 90 such that the substrate 24 side (or substrate 11 side) illustrated in FIG. 2 is a top surface and the top surface becomes flush with the bottom surface of the tableware 90. In addition, though not shown in FIG. 11, devices (such as the processor 3 and the driver circuits 4 and 5) required to configure the circuit illustrated in FIG. 3 are also arranged inside the tableware 90.

When the temperatures of the plurality of thermoelectric elements 10 are individually controlled in a state where liquid or powdery food is on the tableware 90, different temperatures can be given to the food at every position. For example, FIG. 11 shows an example in which the temperatures of the plurality of thermoelectric elements 10 are individually controlled such that the plurality of thermoelectric elements 10 configuring a letter A show relatively high temperature and the other thermoelectric elements 10 show relatively low temperature. Such control allows letters and figures to appear on the surface of food, and therefore a food display can be realized according to the tableware 90 of the present invention.

The invention claimed is:

1. A hot-cold tactile presentation device comprising:
   a plurality of thermoelectric elements arranged in a matrix by placing the thermoelectric elements side by side along a first and a second direction respectively;
   a plurality of first row lines each extending in only the first direction;
   a plurality of column lines each extending in only the second direction; and
   a plurality of second row lines each extending in only the first direction, wherein
   the plurality of first row lines are each connected to one end of each of the plurality of thermoelectric elements that align in the first direction,
   the plurality of second row lines are each connected to the one end of each of the plurality of thermoelectric elements that align in the first direction, and
   the plurality of column lines are each connected to an other end of each of the plurality of thermoelectric elements that align in the second direction.

2. The hot-cold tactile presentation device according to claim 1, wherein the plurality of thermoelectric elements are arranged at intervals on a flexible substrate.

3. A wearable terminal comprising:
   the hot-cold tactile presentation device according to claim 1.

4. A wearable terminal comprising:
   the hot-cold tactile presentation device according to claim 1;
   a first driver circuit that applies one of a power supply potential and a ground potential to one of a first row line of the plurality of first row lines connected to one of the plurality of thermoelectric elements and a second row line of the plurality of second row lines connected to the one of the plurality of thermoelectric elements; and
   a second driver circuit that applies the other of the power supply potential and ground potential to a column line of the plurality of column lines connected to the one of the plurality of thermoelectric elements.

5. The wearable terminal according to claim 4, further comprising:
   a processor that determines a temperature pattern based on a state detected by a sensor or information received from a network service, and controls the first and second driver circuits according to the determined temperature pattern.

6. The wearable terminal according to claim 5, wherein the processor determines, in response to detecting a predefined scratch motion with the sensor, a pattern that can simultaneously give cold and hot stimuli to a user as the temperature pattern.

7. An itch-suppressing device comprising:
   the hot-cold tactile presentation device according to claim 1.

8. An icing device comprising:
   the hot-cold tactile presentation device according to claim 1.

9. A massage device comprising:
   the hot-cold tactile presentation device according to claim 1.

10. An oral retainer comprising:
    the hot-cold tactile presentation device according to claim 1.

11. A tableware comprising:
    the hot-cold tactile presentation device according to claim 1.

12. A hot-cold tactile presentation device comprising:
    a plurality of thermoelectric elements arranged in a matrix by placing the thermoelectric elements side by side along a first and a second direction respectively;
    a plurality of first row lines each extending in the first direction;
    a plurality of column lines each extending in the second direction; and
    a plurality of first diodes that are provided corresponding to each of the plurality of thermoelectric elements, a cathode of each of the plurality of first diodes being connected to one end of a corresponding thermoelectric element of the plurality of thermoelectric elements, wherein
    the plurality of first row lines are each connected, via a corresponding first diode of the plurality of first diodes, to the one end of each of the plurality of thermoelectric elements that align in the first direction, and the plurality of column lines are each connected to an other end of each of the plurality of thermoelectric elements that align in the second direction.

13. The hot-cold tactile presentation device according to claim 12, further comprising:
a plurality of second row lines each extending in the first direction, wherein
the plurality of second row lines are each connected to one end of each of the plurality of thermoelectric elements that align in the first direction.

14. The hot-cold tactile presentation device according to claim 13, further comprising:
a plurality of second diodes that are provided corresponding to each of the plurality of thermoelectric elements, an anode of each of the plurality of second diodes being connected to one end of a corresponding thermoelectric element of the plurality of thermoelectric elements, wherein
the plurality of second row lines are each connected, via a corresponding second diode of the plurality of second diodes, to one end of each of the plurality of thermoelectric elements that align in the first direction.

* * * * *